US00PP09163P

United States Patent [19]

Dehan

[11] Patent Number: Plant 9,163

[45] Date of Patent: Jun. 13, 1995

[54] ASTER PLANT NAMED 'SUNGAL'

[75] Inventor: Klara Dehan, Holon, Israel

[73] Assignee: Danziger- "Dan" Flower Farm, Post Beit Dagan, Israel

[21] Appl. No.: 291,700

[22] Filed: Aug. 16, 1994

[51] Int. Cl.[6] ..... A01H 5/00
[52] U.S. Cl. ..... Plt./68.1
[58] Field of Search ..... Plt. 68.1

*Primary Examiner*—James R. Feyrer
*Attorney, Agent, or Firm*—Foley & Lardner

[57] ABSTRACT

A new and distinct cultivar of aster plant named Sungal, characterized by its violet ray floret color and yellow disc florets; generally cup-shaped single flowers; strong stems; excellent branching; producing many side branches having an abundance of flowers; early flowering; and excellent flower keeping quality.

1 Drawing Sheet

The present invention comprises a new and distinct cultivar of Aster plant, botanically known as *Aster ericoides,* hereinafter referred to by the cultivar name Sungal.

The new cultivar was originated from a cross made in a controlled breeding program by the inventor Klara Dehan in Mishmar Hashiva, Israel.

Both the female, or seed, and the male, or pollen parents were cultivars of *Aster ericoides* which are unknown at this time. Both parents are proprietary lines used exclusively for breeding.

Sungal was discovered and selected by the inventor as a flowering plant within the progeny of the stated cross in a controlled environment in Mishmar Hashiva, Israel. Asexual reproduction of the new cultivar by leaf cuttings performed by the inventor at Mishmar Hashiva, Israel has demonstrated that the combination of characteristics as herein disclosed for the new cultivar are firmly fixed and retained through successive generations of asexual reproduction.

Sungal has not been observed under al possible environmental conditions. The phenotype may vary somewhat with variations in environment such as temperature, light intensity and daylength, without, however, any variation in genotype. The following observations, measurements and values described the new cultivar as grown in Mishmar Hashiva, Israel under conditions which closely approximate those generally used in commercial practice.

The following traits have been repeatedly observed and are determined to be basic characteristics of Sungal which in combination distinguish this Aster as a new and distinct cultivar:

1. Violet ray floret color with yellow disc florets.
2. Medium to large diameter, generally cup-shaped flowers.
3. Excellent branching, producing many side branches with many flowers, thereby producing a very floriferous plant.
4. Early flowering.
5. Excellent flower keeping quality.

The new cultivar can be compared to Suntop, disclosed in U.S. Plant Pat. No. 8,159. The violet ray floret colors, although not identical, are fairly close. Sungal is distinguished from Suntop by its better branching and growth habits, its fewer ray floret petals, and its earlier flowering.

The accompanying color photographic drawing illustrates a portion of a typical specimen plant of the new cultivar, with partially open and completely open flowers being illustrated. The flowers are shown enlarged relative to true size. The photo does not accurately depict the true ray floret color for Sungal. However, the color values noted below are correct.

In the following description, color references are made to The Royal Horticultural Society Colour Chart (R.H.S.), except where general colors of ordinary significance are referred to. Color values were taken in the morning in Mishmar Hashiva, Israel.

Classification:

*Botanical.*—*Aster ericoides* Hybrid cv. Sungal.

*Commercial.*—Daisy-like spray or garden variety.

Parentage:

*Male parent.*—Unknown seedling of *Aster ericoides.*

*Female parent.*—Unknown seedling of *Aster ericoides.*

Propagation:

The new cultivar holds its distinguishing characteristics through successive propagations by leaf cuttings.

INFLORESCENCE

A. Capitulum:

*Form.*—Daisy, generally cup-shaped.

*Type.*—Single.

*Diameter across face.*—Approximately 2.0 cm.

B. Corolla of ray florets:

*Color (general tonality from a distance of three meters).*—Violet.

*Color (upper surface).*—87A.

*Color (under surface).*—88C.

*Shape.*—Florets are generally narrow and oblong, with apex rounded, straight to slightly concave.

C. Corolla of disc florets:

*Color (mature).*—Approximately 3C.

*Color (immature).*—Close to 3B.

*Diameter of disc.*—0.8 cm.

D. Flowering period: When field grown in natural season, plants planted in June will flower in September. In winter greenhouse production, preferred culture includes approximately four weeks of long-day treatment after pinching until the stems elongate to approximately 10 cm, followed by short days. From the start of short days, Sungal will flower in 5 weeks in the fall, and 7 weeks in the winter.

E. Reproductive organs:

*Androecium.*—Stamens present on both ray and disc florets and yellow to purple in color; pollen is yellow and found only in the winter season in Israel.

*Gynoecium.*—Present on disc florets; green in color.

PLANT

A. General appearance: Excellent branching results in a great abundance of medium size, shiny violet flowers; medium to tall in height, the main stem reaching a height of 1.0 to 1.2 meters in a fully grown plant.

B. Foliage:

*Color.*—137A.

*Shape.*—Lanceolate, with occasional downward reflexing at the tip.

*Size.*—A typical leaf at upper part of plant is 55 mm long and 4 mm wide; leaves at lower part of plant are larger, being approximately 145 mm in length and 15 mm in width.

*Margin.*—Entire.

*Arrangement.*—Alternate, with angle acute.

I claim:

1. A new and distinct cultivar of aster plant named Sungal, as illustrated and described.

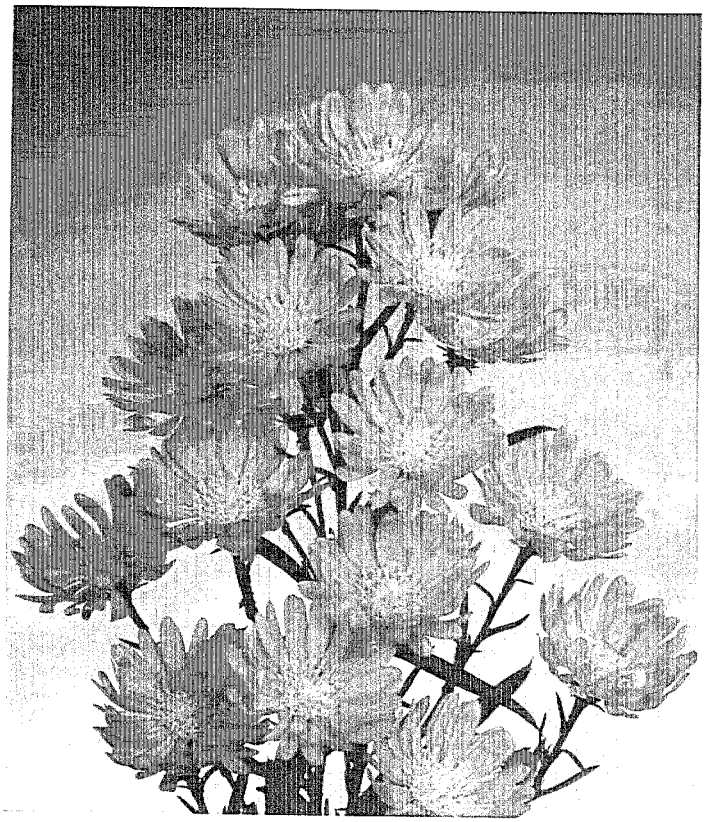

* * * * *